United States Patent [19]

McDonnell

[11] 4,121,589
[45] Oct. 24, 1978

[54] OSTOMY APPLIANCE

[76] Inventor: Roy Edward McDonnell, 15 Miller St., O'Connor, A.C.T., Australia

[21] Appl. No.: 708,852

[22] Filed: Jul. 28, 1976

[30] Foreign Application Priority Data

Aug. 6, 1975 [AU] Australia ............................ 2671/75

[51] Int. Cl.$^2$ .............................................. A61F 5/44
[52] U.S. Cl. ................................................... 128/283
[58] Field of Search ................ 128/283, 295, 285, 154

[56] References Cited

U.S. PATENT DOCUMENTS

| Re. 28,674 | 1/1976 | Guyette | 128/285 |
|---|---|---|---|
| 2,155,285 | 4/1939 | Wilkerson | 128/285 |
| 2,437,019 | 3/1948 | Eich | 128/283 |
| 2,499,414 | 3/1950 | Rabell | 128/285 |
| 2,555,086 | 5/1951 | Guinn | 128/283 |
| 2,639,710 | 5/1953 | Fazio | 128/283 |
| 3,022,786 | 2/1962 | Nalon | 128/283 |
| 3,386,441 | 6/1968 | De Merre | 128/285 X |
| 3,759,260 | 9/1973 | Nolan et al. | 128/283 |

FOREIGN PATENT DOCUMENTS

| 141,439 | 11/1949 | Australia | 128/283 |
|---|---|---|---|
| 77,392 | 3/1954 | Denmark | 128/283 |

*Primary Examiner*—Robert W. Michell
*Assistant Examiner*—Michael H. Thaler

[57] ABSTRACT

An ostomy appliance comprises an attachment portion having an aperture therethrough adapted to register with an opening in the body of a patient and having adhesive on one face thereof adapted to secure the attachment portion to the body of the patient surrounding the opening, the attachment portion being provided on the opposite face thereof with structure for securing a cap member in sealing relationship thereto over the aperture; and a cap member comprising a generally concave body member of rigid or semi-rigid material, the body member containing absorbent material for absorbing drainage and/or discharge from the opening and being provided with structure engaging the attachment portion for securing said cap member to said attachment means. The appliance may further include an absorber member adapted to be inserted into the opening through the aperture in the attachment portion, the absorber member comprising a generally tubular absorption and storage member having inner and outer walls of fluid pervious material, the inner and outer walls being separated by absorbent material, and a flange at one end of the tubular member to retain the absorber member in position in the opening on securing the cap member to the attachment portion.

15 Claims, 12 Drawing Figures

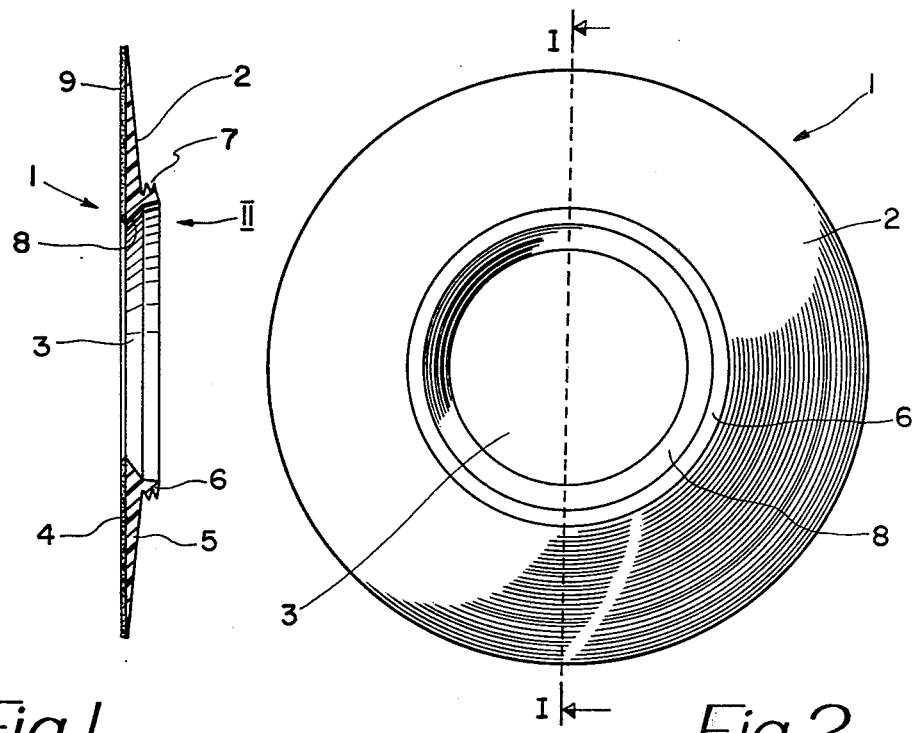
*Fig.1.* *Fig.2.*
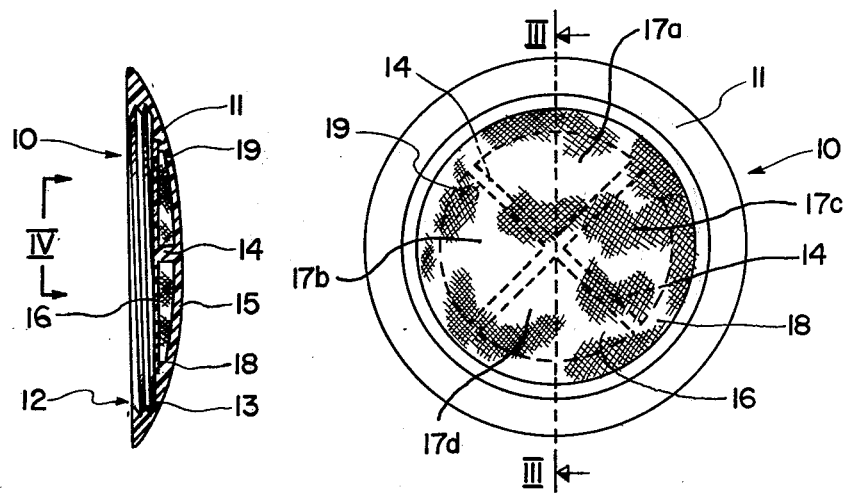
*Fig.3.* *Fig.4.*

OSTOMY APPLIANCE

This invention relates to a surgical appliance for use by patients who have undergone abdominal surgery as a result of which an abdominal opening or stoma has been left in the body.

Such surgical techniques are well known and, by way of example, reference is made to colostomy operations (in which the large intestine is brought through the abdominal wall) and ileostomy operations (in which the large intestine is completely removed and the small intestine is brought through the abdominal wall). In each case, drainage or discharge from the digestive system of the patient takes place through the opening or stoma in the abdominal wall and it is necessary to provide means to receive this drainage or discharge from the stoma which cannot be controlled by the patient.

Many forms of surgical drainage bags or pouches are known, these usually comprising a flexible waterproof bag or pouch which is securely attached to the body of the patient so as to surround the stoma and so receive the drainage or discharge. By way of example, reference is made to Australian Patent Specifications Nos. 411931 and 445414, both of which disclose such flexible waterproof bags or pouches with means for sealing the bag or pouch to the body. As illustrated in these specifications, generally such bags or pouches are secured to the body by means of an adhesive and considerable difficulty, discomfort and skin irritation is often experienced in removing and replacing such appliances both when the bag or pouch is directly attached to the body and when an adhesive attachment means, separate from the bag or pouch, is utilised. Furthermore, difficulties may also arise from leakage of such appliances, particularly between the bag or pouch and the skin of the patient, where the seal is insufficient or incomplete. Such leakage would, of course, cause considerable inconvenience and embarassment to the patient if it occurred while the appliance was being used in public.

Whilst a surgical drainage appliance in the form of a flexible waterproof bag or pouch may be utilised in the collection of liquid or solid drainage from the stoma, it is also important to provide for the control of any gaseous discharge which may occur. Clearly the collection of such gaseous discharge in a bag or pouch as discussed above is not desirable since the resultant inflation of the appliance tends to force it away from the patient's body, thus placing additional strain on the seal or seals between the appliance and the skin of the patient. Australian Patent Specification No. 472114 discloses an appliance for controlled venting of gas and containment of small amounts of waste discharge which consists of a small fluid-tight pouch which is sealed in position around the stoma and which contains an absorbent pad, and a vent aperture in the pouch for exhausting gas from the pouch. Such an appliance is, however, subject to most of the disadvantages discussed above in connection with drainage collection bags or pouches. In particular, as this appliance is secured to the body by means of an adhesive, the problems of application and removal and of incomplete sealing again arise.

It is an object of the present invention to provide a surgical appliance which may be used to receive solid and liquid drainage and/or gaseous discharge from a stoma in the body of a patient and which will provide reliable sealing of the stoma, thereby reducing the possibility of leakage. Such an appliance will be of considerable benefit to the patient since it can be confidently used in public.

According to the present invention, there is provided an appliance for receiving drainage and/or discharge from an opening in the body of a patient, comprising:
attachment means having an aperture therethrough adapted to register with said opening and having adhesive means on one face thereof adapted to secure said attachment means to the body of the patient surrounding said opening, said attachment means being provided in the opposite face thereof with means for securing a cap member in sealing relationship thereto over said aperture; and a cap member comprising a generally concave body member of rigid or semi-rigid material, said body member containing absorbent material for absorbing drainage and/or discharge from said opening and being provided with means engaging said attachment means for securing said cap member to said attachment means.

The device of this aspect of the present invention is particularly intended for use as a temporary drainage device.

In another aspect, the invention provides an appliance which is particularly suitable for continuous use as an appliance for receiving drainage and/or discharge from an opening in the body of a patient comprising:
attachment means having an aperture therethrough adapted to register with said opening and having adhesive means on one fact thereof adapted to secure said attachment means to the body of the patient surrounding said opening, said attachment means being provided on the opposite face thereof with means for securing a cap member in sealing relationship thereto over said aperture;
a cap member comprising a generally concave body member of rigid or semi-rigid material, said body member containing absorbent material for absorbing drainage and/or discharge from said opening and being provided with means engaging said attachment means for securing said cap member to said attachment means;
and an absorber member adapted to be inserted into said opening through said aperture in said attachment means, said absorber member comprising a generally tubular absorption and storage member having inner and outer walls of fluid pervious material, said inner and outer walls being separated by absorbent material, and a flange at one end of said tubular member to retain said absorber member in position in said opening on securing said cap member to said attachment means.

Also separately provided by the present invention are (a) an appliance for receiving drainage and/or discharge from an opening in the body of a patient, comprising a generally concave body member of rigid or semi-rigid material, said body member containing absorbent material for absorbing said drainage and/or discharge from said opening and being provided with means for engaging attachment means surrounding said opening in sealing relationship thereof.

(b) an absorption appliance for insertion into an opening in the body of a patient, comprising a generally tubular absorption and storage member having inner and outer walls of fluid pervious material, said inner and outer walls being separated by absorbent material and means at one end of said tubular member to retain the appliance in position in said opening.

As previously described, the appliance in accordance with the present invention contains absorbent material. Any well-known material used in the medical field as an absorbent may be used in accordance with the present invention. In particular, the use of activated carbon, charcoal or a similar absorbent material, either alone or in association with other materials, is preferred as a gas absorbent in view of the absorption of odorous gases by this material. Clay, lint or crepe-like paper may be used as a liquid or semi-solid absorbent.

Further features of the present invention will be apparent from the accompanying drawings which illustrate, by way of example only, a preferred embodiment of this invention. In the drawings:

FIG. 1 is a sectional side elevation, taken along line I—I of FIG. 2 of an attachment means in accordance with this preferred embodiment of the present invention;

FIG. 2 is a plan view of the attachment means of this embodiment, taken in the direction of the arrow II in FIG. 1;

FIG. 3 is a sectional side elevation, taken along line III—III of FIG. 4, of a cap member in accordance with this preferred embodiment of the present invention;

FIG. 4 is a plan view of the cap member of this embodiment, taken in the direction of the arrow IV in FIG. 3;

Figures 10, 11:
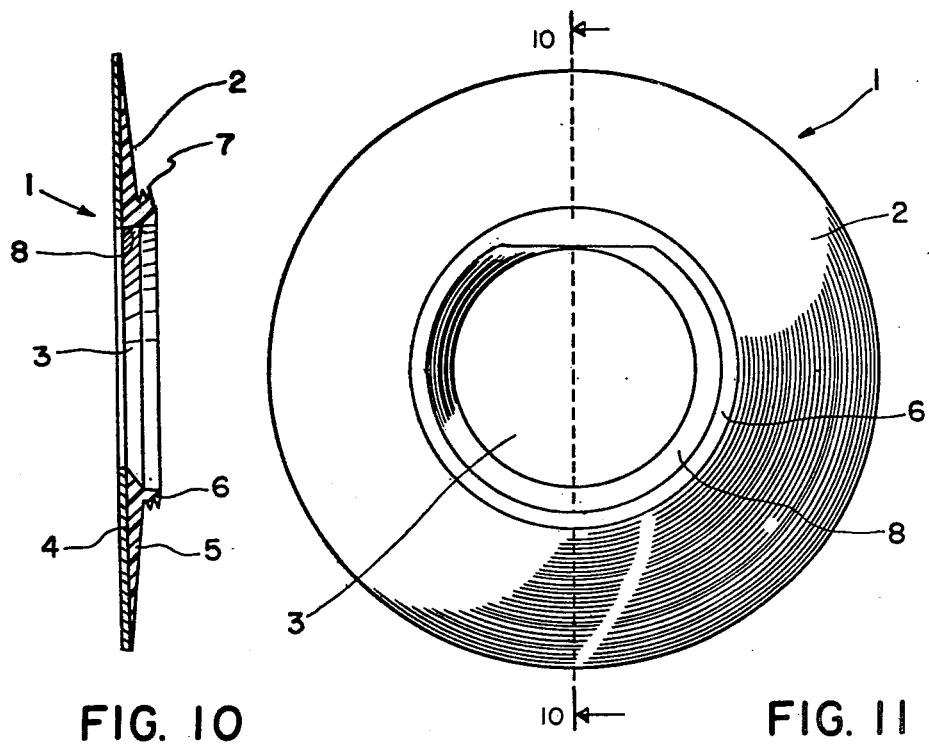

FIGS. 10 and 11 are a sectional side elevation and plan view, respectively, of an alternate embodiment of the attachment means shown in FIGS. 1 and 2, FIG. 10 being taken along line 10—10 of FIG. 11.

Referring firstly to FIGS. 1 and 2, the attachment means 1 comprises a generally flat, circular disc member 2 having a circular aperture 3 centrally located therein to register with the stoma or similar opening in the body of the patient. Preferably, the attachment means 1 is formed from rigid or semi-rigid plastics material such as low density polypropylene or ethylene vinyl acetate or from thermoplastic elastomeric material and is tapered towards the outer circumference thereof as shown in FIG. 1. Adhesive material (9) is provided on the side 4 of the disc member 2 and suitable non-toxic and non-irritating adhesive materials are known. Extending outwardly from the side 5 of the disc member 2, and surrounding the aperture 3, is a cylindrical portion 6 having an external thread 7 formed thereon to sealingly engage a cap member as described hereinafter. The interior surface of the portion 6 is formed with an annular, inwardly inclined seating flange 8 for seating an absorbing member in the manner also described hereinafter.

As shown in FIGS. 3 and 4, the cap member 10 consists of a generally concave body member 11, formed of rigid or semi-rigid plastics material such as low density polypropylene or ethylene vinyl acetate or of thermoplastic elastomeric material having at or towards its open end 12, means 13 for securing the body member to attachment means surrounding a stoma or opening in the abdominal wall of a patient. As illustrated, means 13 comprises a thread in the inner wall of body member 11 which is intended to engage the radially outwardly extending thread 7 on the attachment means 1.

Remote from the open end 12, body member 11 is formed with radial rib members 14 which extend axially from the closed end 15 of the body member. Rib members 14 extend between the closed end 15 and a perforated transverse retaining member 16 so as to divide the area enclosed by the closed end 15, the sides of body member 11 and the retaining member 16 into four compartments 17a, 17b, 17c, 17d containing suitable absorbent material, particularly gas absorbing material. Retaining member 16 may be constructed as a disc of semi-rigid plastics mesh.

As illustrated, retaining member 16 may be secured in position after the absorbent material has been placed in position in compartments 17 as desired by heat or ultrasonic welding the edge of the member 16 onto a circumferential flat 18 in the inner wall of the body member. A pin (not shown) may also be inserted through the retaining member 16 into a suitable hole at the junction of the rib members 14.

The absorbent materials used in the cap member 10 may be a combination of gas absorbents such as activated carbon and liquid or semi-solid absorbents such as clay. In the embodiment shown in FIGS. 3 and 4, the member has a particular preferred orientation in use which may be suitably designated, for example, by moulding or otherwise applying the word "top" in an appropriate position on the member. Compartment 17d may then be used to hold clay as the liquid or semi-solid absorbent as liquid or semi-solid drainage or discharge will tend to collect at the lower portion of the appliance. Compartments 17a, 17b and 17c may thus be used to contain activated carbon as the gas absorbent.

Preferably, air vent 19 is provided in the closed end 12 of the body member 11 to allow purified gases to escape and thereby avoid build up of gas pressure within the cap member.

In an alternative embodiment of the cap member, this member may consist of a generally concave body member having at or towards its open end means such as an internal thread for securing the body member to attachment means surrounding an opening in the body of the patient, as shown in FIGS. 3 and 4. Preferably, air vents are also provided in the closed end of the body member as described above. In this embodiment, the absorbent material is contained within a disposable, fluid pervious bag or pouch, such as a nylon mesh bag or pouch, which is dimensioned so as to be contained within the concave body member and held in position therein on securing the body member to the attachment.

Figure 8:
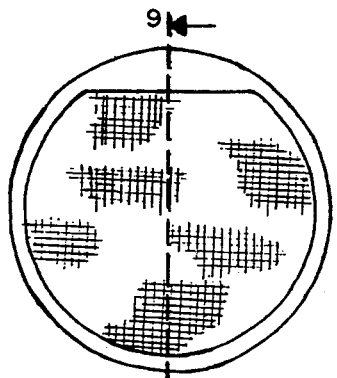
FIG. 8 is an elevational view of the fluid pervious bag used in the present invention.
Figure 9:
FIG. 9 is a cross-sectional view of the fluid pervious bag in FIG. 8 taken along line 9—9 of FIG. 8.

Preferably the disposable bag or pouch is generally disc-shaped and sufficiently rigid as to be shape retaining. It may contain only a gas absorbent such as activated carbon. This bag or pouch may, however, be constructed so as to contain a gas absorbent such as activated carbon in one portion thereof and a liquid or semi-solid absorbent such as clay in a separate portion thereof. In this latter construction, the body member and bag or pouch are preferably constructed so as to provide a specific orientation of the bag or pouch so that, in use, the portion containing the gas absorbent is uppermost. This specific orientation may be attained by forming a flat in the perimeter of an otherwise disc-shaped bag or pouch (see FIGS. 8 and 9) with a corresponding internal configuration in the body member (as shown in FIGS. 10 and 11).

It will be apparent that this embodiment of the cap member has distinct economic advantages since only the disposable bag or pouch, which can be simply and economically made, needs to be replaced in use.

Figure 5:
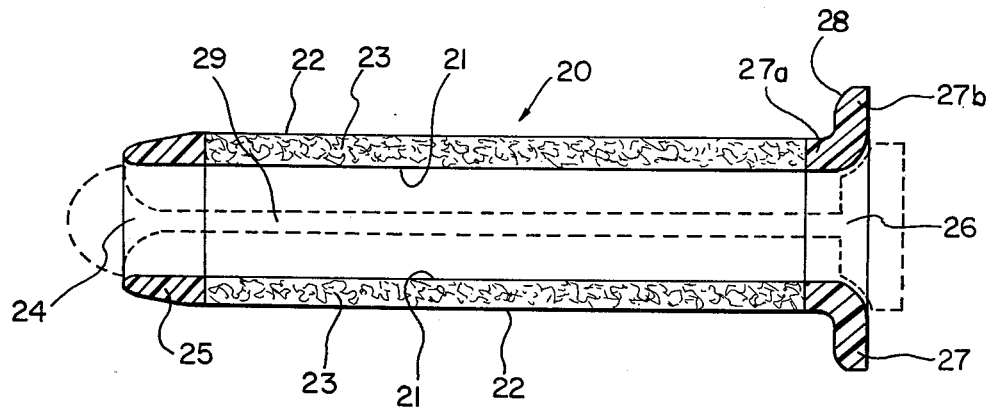
FIG. 5 is a sectional side elevation of an absorber member in accordance with this preferred embodiment of the present invention.

Absorber member 20, illustrated in FIG. 5, is adapted for insertion into the stoma or similar opening in the body to operate as a liquid and solid absorption and storage device. Member 20 consists of inner and outer tubular walls, 21 and 22 respectively, of non-toxic fluid-pervious plastics material such as Acropor, an acrylonitrile polyvinylchloride copolymer membrane from Gelmar Instrument Company. Alternatively, walls 21 and 22 may be formed of other membrane material perforated with holes of suitable size, or of mesh material. Absorbent material 23 is positioned between the walls 21 and 22 and preferably consists of liquid absorbent material such as flocculent clay, absorbent paper or lint. At one end 24 of the walls 21, 22, a tapered annular nose portion 25 is formed, nose portion 25 being preferably constructed of semi-rigid material (for example, low density polypropylene or ethylene vinyl acetate) or thermoplastic elastomeric material so as to retain the end 24 of the member 20 open in use in the body to receive liquid and solid drainage into the interior of the member. The other end 26 of the member 20 is provided with an annular sealing flange 27 of rigid or semi-rigid plastics material which may be the same material as that of nose portion 25. Sealing flange 27 is formed with a first annular portion 27a connecting with the walls 21 and 22 and having the same external diameter as that of the outer wall 22, and the same internal diameter as that of the inner wall 21, and a second portion 27b remote from the walls 21 and 22. The portion 27b is radially outwardly directed and is dimensioned so as to be received within the aperture 3 of the attachment means 1 (see FIG. 3) with an inclined surface 28 formed thereon seating on inclined surface 8 of the attachment means.

Figure 5A:
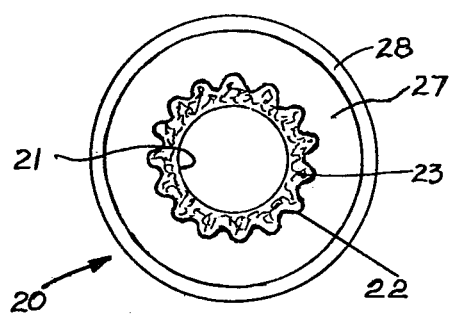
FIG. 5a is a cross-sectional view of the absorber member of FIG. 5.

Since the walls 21 and 22 of the member 20 are not structurally rigid, it is preferred that an inserting finger, depicted in dotted outline at 29 in FIG. 5, be used in inserting member 20 into the opening in the body of the patient. Apart from providing the desired rigidity, the inserting finger 29 is preferably formed with a tapered nose portion to co-operate with the tapered nose portion 25 of the member 20 and allow the absorber member to be inserted, for instance, into the colon of the patient without damage to the colon wall. The inserting finger is then retracted leaving the absorber member in place. When so used, the inner tubular wall of the member 20 allows the liquid component of the drainage (such as the fluid chyme) to pass into and be absorbed by the material 23, while the solid component of the drainage (such as the faeces) is retained within the inner tube in a form for subsequent disposal. Liquid which is absorbed by the absorbent material 23 may be further transferred through the outer wall 22 to the colon wall and thereby returned to the blood stream. Preferably, the outer wall 22 is corrugated longitudinally to assist transfer of the absorber liquid to the colon wall and, in addition, to assist in withdrawal of the absorber member after use (see FIG. 5a).

Figure 6:
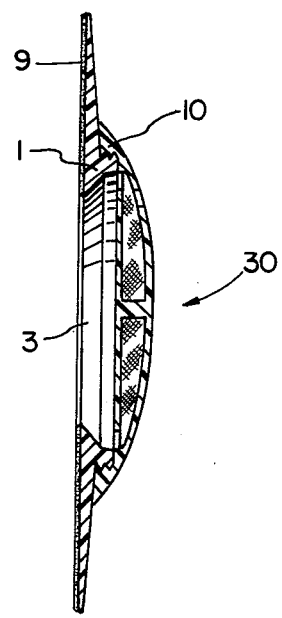
FIG. 6 is a sectional side elevation of one appliance in accordance with this preferred embodiment.

The appliance in accordance with the present invention which is depicted in FIG. 6 of the drawings is particularly intended for use as a temporary drainage device, that is for use in situations where, for example, the patient intends to be in a public place for a limited period of time and the anticipated amount of liquid or solid drainage from the stoma is small. Primarily then, the appliance 30 is designed as a gas absorber device, however provision is made for the absorption of the anticipated liquid and solid drainage. Appliance 30 consists of an attachment means 1 as described with reference to FIGS. 1 and 2, which is adapted to be affixed to the body of the patient with the aperture 3 in register with the stoma or other opening, and a cap member 10 as described with reference to FIGS. 3 and 4, threadingly engaged therewith to seal the appliance. Although not illustrated, it will be appreciated that sealing washers of suitable material may be used between means 1 and member 10 to assist in sealing of the opening, and further absorber members such as lint discs may be positioned in aperture 3 prior to assembly of the appliance 30.

Figure 7:
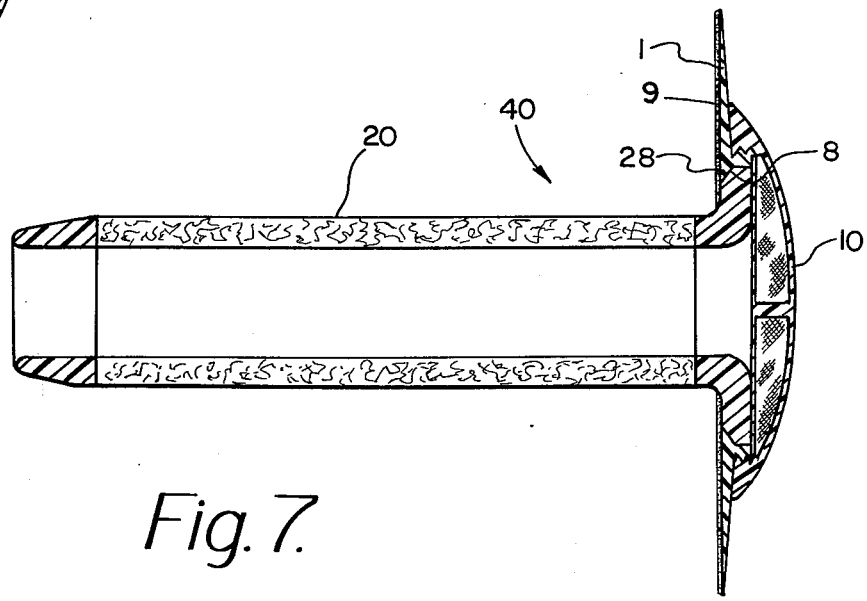
FIG. 7 is a sectional side elevation of an alternative appliance in accordance with this invention.

The appliance 40 illustrated in FIG. 7 is intended for use as a full drainage and discharge absorption device in place of the known externally applied, flexible waterproof bags or pouches as described above. As with the appliance 30 shown in FIG. 6, appliance 40 consists of an attachment means 1 as described above adapted to be affixed to the body of the patient surrounding the opening, and a cap member 10 also as described above. In appliance 40, however, an absorber member 20 is inserted into the opening in the patient's body through the aperture in the attachment means 1 so that the inclined surfaces 8 and 28 seat against each other. The threaded engagement of the cap member 10 with the attachment then seals the device 40, if desired with the additional use of sealing washers and additional absorber members such as lint discs between the member 20 and the cap member 10, thereby sealingly retaining the absorber member 20 in place and providing for complete absorption of liquid, solid and gaseous drainage and discharge from the opening in the patient's body.

It will be appreciated from the foregoing, that since the cap member 10 of the appliances of FIGS. 6 and 7 is simply screwed onto the attachment means, it may be readily removed for replacement of the cap member 10 and the absorber member 20 without disturbing the adhesion of the attachment means 1 to the patient's body, thus avoiding disruption of the sealing of the opening. It will, however, be appreciated that other forms of engagement between the cap member 10 and the attachment means 1 may be used, in particular a "snap-fit" type of engagement.

It will be appreciated that the appliance of this invention is of simple, economical construction which enables it to be used conveniently by a patient, and for used absorption members to be disposed of simply after use. Of course, many modifications and variations may be made to the appliances illustrated in the drawings without departing from the present invention, and all such modifications and variations are intended to be included within the scope of this invention.

The claims defining the invention are as follows:

1. An appliance for receiving drainage and discharge from an opening in the body of a patient, comprising:
attachment means having two opposite faces and an aperture therethrough adapted to register with said opening and having adhesive means on one face thereof adapted to secure said attachment means to the body of the patient surrounding said opening, said attachment means being provided on the opposite face thereof with means for securing a cap member in sealing relationship thereto over said aperture;

a cap member comprising a generally concave body member of semi-rigid material, said body member containing absorbent material for absorbing drainage and discharge from said opening and being provided with means engaging said attachment means for securing said cap member to said attachment means;

and an absorber member adapted to be inserted into said opening through said aperture in said attachment means, said absorber member comprising a generally tubular absorption and storage member having inner and outer walls of fluid pervious material, said inner and outer walls being separated by absorbent material, and a flange at one end of said tubular member to retain said absorber member in position in said opening on securing said cap member to said attachment means.

2. An appliance according to claim 1, wherein said attachment means comprises a substantially flat body of semi-rigid plastic material, and said means for securing a cap member comprises an externally-threaded cylindrical member surrounding said aperture therein.

3. An appliance according to claim 2 wherein said externally-threaded cylindrical member has an inwardly inclined annular seating flange formed therein.

4. An appliance according to claim 1 further comprising a retaining member spaced from a concave wall portion of said concave body member, for retaining said absorbent material in said body member between the concave wall of said member and said retaining member.

5. An appliance according to claim 4 wherein a plurality of radial rib members extend axially from the concave wall of the body member to said retaining member to form a plurality of compartments for said absorbent material.

6. An appliance according to claim 5 wherein at least one of said compartments is provided with a vent hole.

7. An appliance according to claim 4, wherein said absorbent material includes activated carbon.

8. An appliance according to claim 4, wherein said means for engaging attachment means comprises an internal thread formed in the body member.

9. An appliance according to claim 1, wherein an annular, tapered nose portion of semi-rigid material is provided at the end of said tubular member remote from said one end.

10. An appliance according to claim 9, wherein said flange is dimensioned to be received within said aperture in the attachment means.

11. An appliance according to claim 9, wherein said outer wall is longitudinally corrugated.

12. An appliance according to claim 9, wherein said absorbent material separating said inner and outer walls comprises one of the elements selected from the group consisting of clay, absorbent paper and lint.

13. An appliance according to claim 1 wherein said absorbent material is contained within a generally disc-shaped disposable, fluid pervious bag or pouch received within said body member, and said body member is provided with at least one vent hole.

14. An appliance according to claim 13 wherein said bag or pouch and said body member include cooperating means, such that said bag or pouch fits within said body member in only one specific orientation.

15. An appliance according to claim 14, wherein said bag or pouch contains a gas absorbent material in one portion thereof and a liquid or semi-solid absorbent material in a separate portion thereof.

* * * * *